US00PP16770P2

(12) United States Plant Patent
Lim

(10) Patent No.: US PP16,770 P2
(45) Date of Patent: Jul. 4, 2006

(54) SHRUB ROSE PLANT NAMED 'BAISET'

(50) Latin Name: *Rosa hybrida*
Varietal Denomination: BAIset

(75) Inventor: Peter P. Lim, Yamhill, OR (US)

(73) Assignee: Bailey Nurseries, Inc., St. Paul, MN (US)

( * ) Notice: Subject to any disclaimer, the term of this patent is extended or adjusted under 35 U.S.C. 154(b) by 90 days.

(21) Appl. No.: 11/015,025

(22) Filed: Dec. 20, 2004

(51) Int. Cl.
*A01H 5/00* (2006.01)

(52) U.S. Cl. ..... Plt./102

(58) Field of Classification Search ..... Plt./102
See application file for complete search history.

*Primary Examiner*—Kent Bell
*Assistant Examiner*—Annette H Para
(74) *Attorney, Agent, or Firm*—Buchanan Ingersoll PC

(57) ABSTRACT

A new and distinct variety of landscape shrub rose plant is provided which forms on a substantially continuous basis attractive semi-double bright fuchsia pink blossoms that change to apricot yellow and near white at the center. The plant exhibits a dense spreading growth habit that makes it an ideal ground cover. The new plant also is well suited for growing as a mass planting. The medium to dark green semi-glossy foliage contrasts nicely with the blossom coloration. High tolerance to Black Spot and Powdery Mildew is displayed. The plant can be grown to advantage to provide attractive ornamentation in parks and gardens.

2 Drawing Sheets

Botanical commercial classification: *Rosa hybrida*/Shrub Rose Plant.

Varietal denomination: cv. 'BAIset'.

SUMMARY OF THE INVENTION

The new variety of *Rosa hybrida* landscape shrub rose plant was created at Yamhill, Oreg., U.S.A., during 1996 by artificial pollination wherein two parents were crossed which previously had been studied in the hope that they would contribute the desired characteristics. The female parent (i.e., the seed parent) was an unnamed and unreleased *Rosa hybrida* shrub rose plant from my breeding program designated '95BNIab' (non-patented in the United States). The male parent (i.e., the pollen parent) was an unnamed and unreleased *Rosa hybrida* shrub rose plant form my breeding program designated '91X917' (non-patented in the United States). The parentage of the new variety can be summarized as follows:

'95BNIab'×'91X917'.

The seeds resulting from the above pollination were sown and plants were obtained which were physically and biologically different from each other. Selective study resulted in the identification during 1999 of a single plant of the new variety having the distinctive ornamental characteristics hereafter described.

It was found that the new variety of the present invention:

(a) exhibits a dense spreading growth habit, (b) forms in clusters on a substantially continuous basis attractive semi-double bright fuchsia pink blossoms that change to apricot yellow and near white at the center, (c) forms medium green to dark green semi-glossy foliage, (d) displays high tolerance to Black Spot and Powdery Mildew; and (e) is particularly well suited for growing as attractive ornamentation in parks and gardens.

The blossoms are an attractive blend of pink-yellow coloration. The blossom coloration passes through several color changes. Red changes to fuchsia pink blended with apricot yellow and near white. The blossom coloration contrasts nicely with the medium green to dark green foliage. The new variety perfroms well in U.S.D.A. Hardiness Zone Nos. 4 to 9.

The new variety well meets the needs of the horticultural industry. It can be grown to advantage where attractive ornamentation is desired, such as in parks and gardens. The dense spreading growth habit makes it an ideal ground cover and makes it well suited for growing in a mass planting.

The new variety can be readily distinguished from other varieties including its parental varieties. More specifically, the '95BNIab' parent forms yellow-pink double blossoms in clusters having approximately 23 petals. '91X917' forms forms yellow-pink single blossoms in clusters having 5 petals, and light green foliage.

The new variety of the present invention also readily can be distinguished from the 'Honeysweet' (non-patented in the United States) and 'BAIsme' (non-patented in the United States) varieties. More specifically, the 'Honeysweet' variety exhibits an upright growth habit, forms darker green foliage, and forms larger blossoms, and the 'BAIset' variety exhibits an upright-rounded growth habit, forms darker green and glossy foliage, and forms larger blossoms. There are also differences in blossoms coloration.

The new variety has been found to undergo asexual propagation by budding on an understock beginning in August 1997 and by the rooting of cuttings. 'Dr. Huey' rootstock (non-patented in the United States) was used during the budding. Such asexual propagation by these techniques at Yamhill, Oreg., U.S.A., St. Paul, Minn., U.S.A., and at Phoenix, Ariz., U.S.A., has shown that the characteristics of the new variety are stable and are strictly transmissible by such asexual propagation from one generation to another. Accordingly, the new variety reproduces true to type. The new variety grows well on its own roots.

Initially the new plant was designated '96A33', and was evaluated during 2002 and 2003 under the designation 'O2R511'. The new variety subsequently has been named 'BAIset', and currently is being marketed while using the GARDEN PATH and SUNRISE SUNSET trademarks.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately two and three years of age, and were being grown outdoors at St. Paul, Minn., U.S.A. and Yamhill, Oreg., U.S.A. during the 2003 and 2004 seasons.

DETAILED DESCRIPTION

Figure 1:
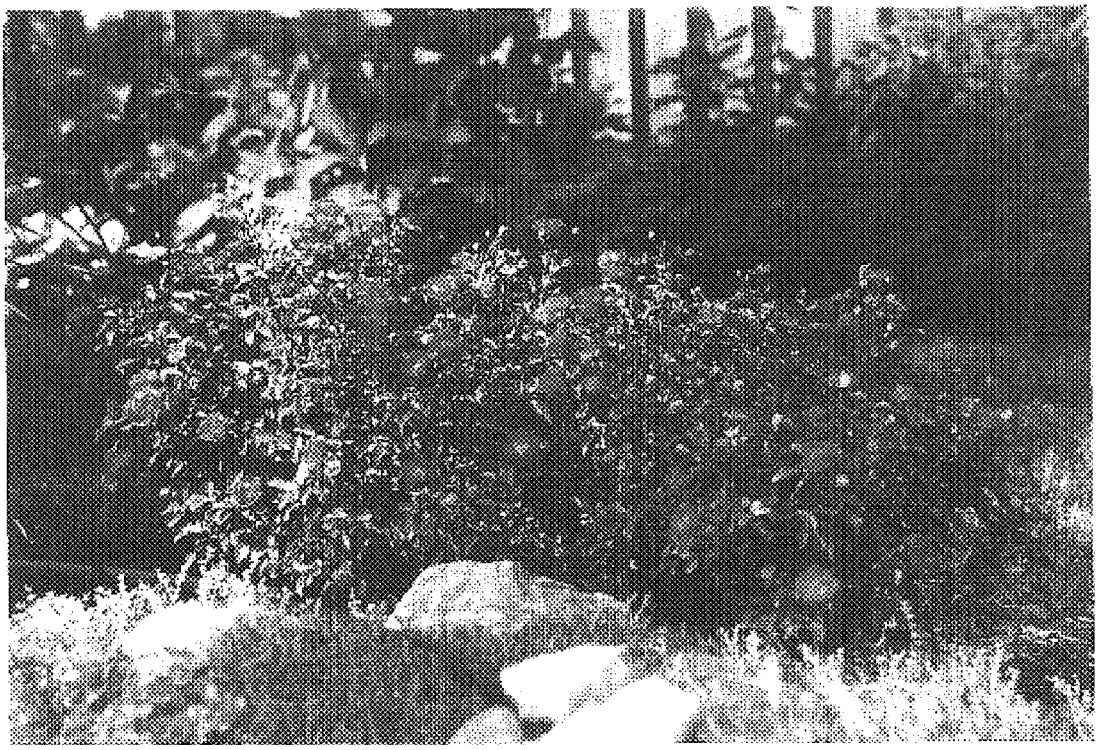
FIG. 1 illustrates flowering plants of the new variety while growing in a garden setting.
Figure 2:
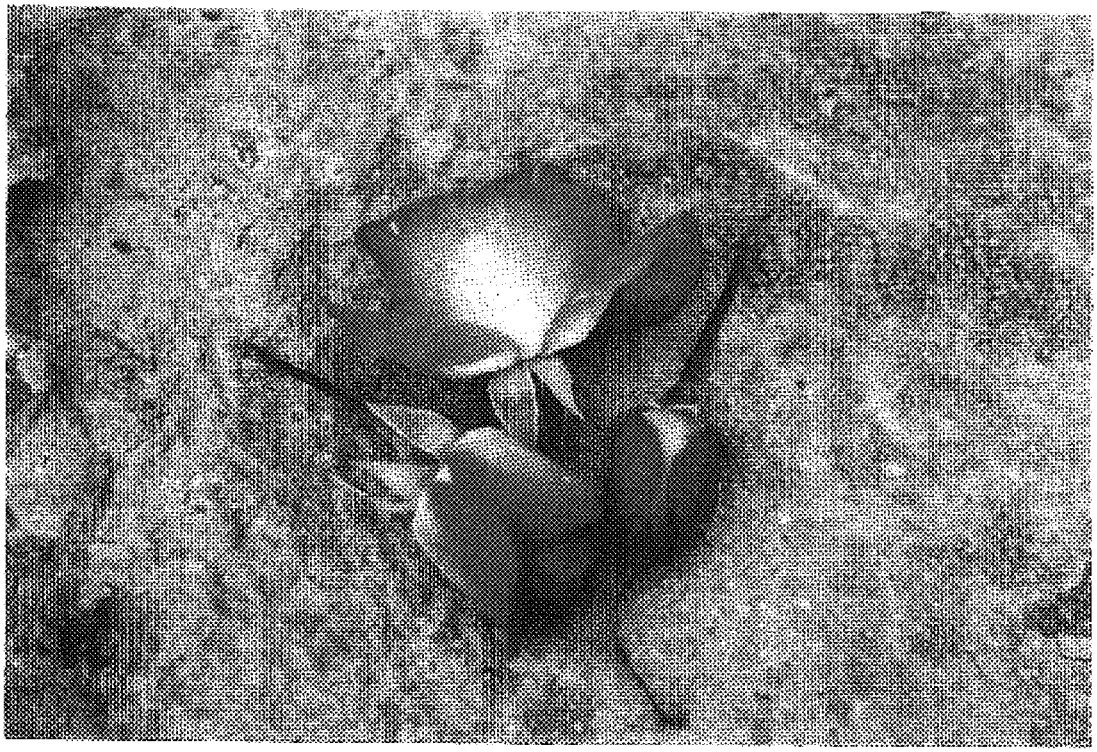
FIG. 2 illustrates a close view of an opening bud and two newly opened flowers.
Figure 3:
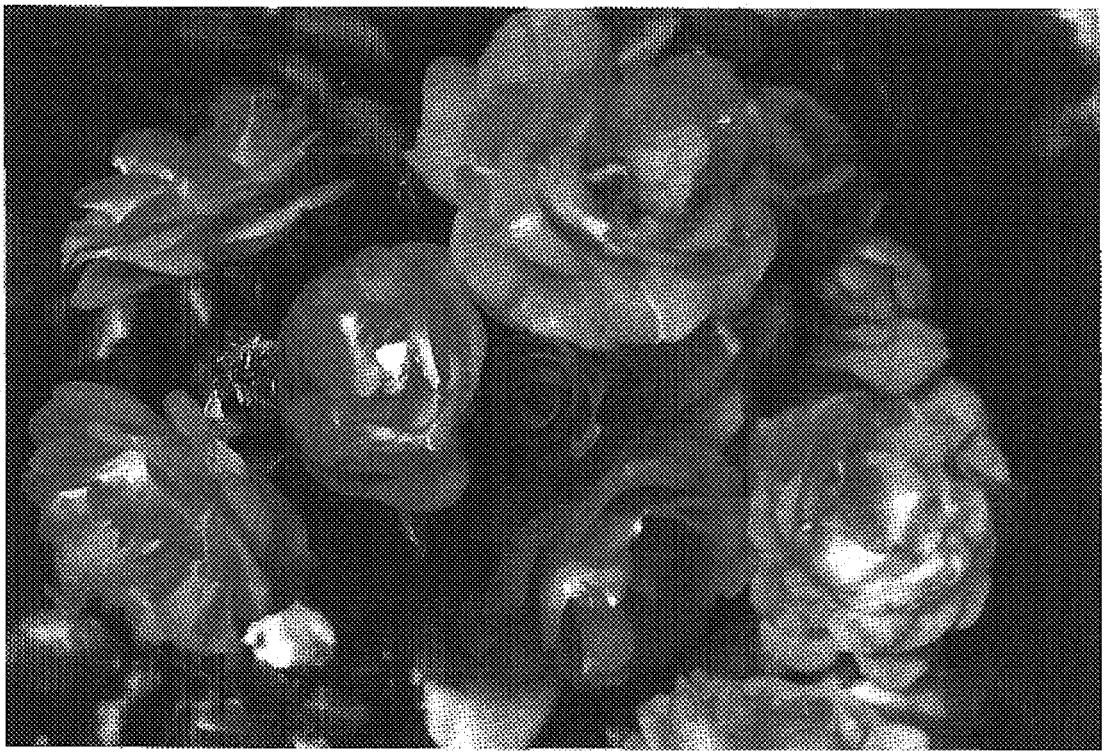
FIG. 3 illustrates an array of blossoms in various stages of maturity as well as the medium green to dark green semi-glossy foliage. The apricot yellow center blossom coloration of mature blossoms is shown in some instances.
Figure 4:
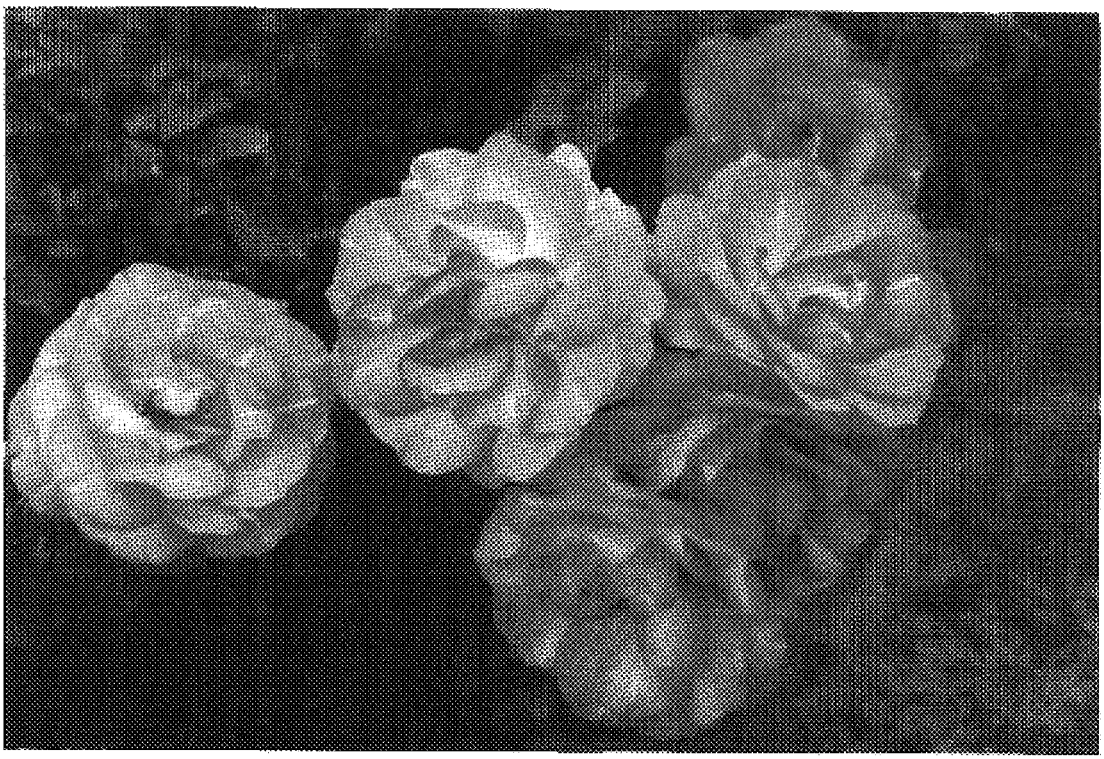
FIG. 4 illustrates a further array of the attractive blossoms of the new variety.

The chart used in the identification of the colors is that of The Royal Horticultural Society (R.H.S. Colour Chart). Common color terms are to be accorded their ordinary dictionary significance. The description is based on the observation of two and three year-old plants while grown outdoors on their own roots during June 2003 at Yamhill, Oreg., U.S.A., and July 2004 at St. Paul, Minn., U.S.A.

Botanical classification: *Rosa hybrida*, var. 'BAIset'.
Class: Landscape Shrub.
Plant:
- *Height.*—Approximately 60 to 90 cm on average at the end of the growing season.
- *Width.*—Approximately 50 to 60 cm on average at the end of the growing season.
- *Habit.*—Dense and spreading.

Branches:
- *Color.*—Young stems: Green Group 138A suffused with Greyed-Purple Group 185B. Adult wood: Green Group 137B with streaks of Grey-Brown Group 199A.
- *Thorns.*—Size: commonly approximately 5.5 mm in length on average. Color: Red-Purple Group 59B.

Leaves:
- *Stipules.*—Generally parallel with the auricle facing outward.
- *Petioles.*—Upper surface: Green Group 137B and 137C commonly with Greyed-Purple Group 187B near the stipule. Under surface: commonly between Green Group 137A and 137B.
- *Leaflets.*—Number: 3, 5 (most often), and 7. Shape: ovate with a rounded base and an acuminate tip. Margin: serrulate. Texture: bears a satiny finish. General appearance: medium to dark green with semi-glossy surface when mature. Color (young foliage): Upper surface: Greyed-Purple Group 183A. Under surface: Greyed-Purple Group 183B. Color (adult foliage): Upper surface: Green Group 137A. Under surface: Yellow-Green Group 146A commonly suffused with Greyed-Purple Group 183A at the margin.

Inflorescence:
- *Number of flowers.*—Typically in clusters, and commonly approximately 5 flowers on average per stem.
- *Peduncle.*—Approximately 5.5 cm in length on average, Green Group 138A tinted with Greyed-Purple Group 185A in coloration; and commonly bears somewhat evenly spread prickles.
- *Sepals.*—Upper surface: Green Group 137A with some streaking of Greyed-Purple Group 184A, and commonly with pubescence. Under surface: Green Group 138A commonly blended with Greyed-Purple Group 184B, and with pubescence at the margin. Size: approximately 2.25 cm in length on average.
- *Buds.*—Shape: pointed. Size: medium. Length: approximately 2.5 cm on average. Diameter: approximately 1.75 cm on average. Color: Upper petal surface: Red Group 45B and Red Group 46B suffused with Red-Purple Group 70B. Under petal surface: Red Group 45B suffused with Red-Purple Group 70A and 70B blending to Red-Purple Group 69C and Yellow Group 4A with the inner petals commonly displaying less blending and being primarily Red Group 45A and Yellow Group 4B.
- *Flower.*—Shape: semi-double. Diameter: approximately 5.5 cm on average. Color (when opening begins): Upper surface: Red Group 45B suffused with Red-Purple Group 70A and 70B blending to Red-Purple Group 69C and White Group 155D with the inner petals commonly displaying less blending and being primarily Red Group 45A and Yellow Group 4A. Under surface: Red Group 45B suffused with Red-Purple Group 70A and 70B blending to Red-Purple Group 69C and White Group 155A with the inner petals commonly displaying less blending and being primarily Red Group 45A and Yellow Group 4A. Color (when blooming): Upper surface: Red-Purple Group 66C blended with Red-Purple Group 68A and 68B and suffused with Yellow Group 11B, 11C, and 11D. Under surface: between Red-Purple Group 70B and 70C suffused with Purple Group 75B and 75C blending to Yellow-White Group 158D. Color (at end of blooming): Upper surface: between Red-Purple Group 68C and 68D and Red-Purple Group 70A and primarily at the margin blending to White Group 155C and 155D. Under surface: Red-Purple Group 70D and primarily at the margin blending to White Group 155C. Color (basal petal spot): Yellow Group 4A. Fragrance: slight rose. Lasting quality: the blossoms commonly last approximately 5 to 7 days on average depending upon the temperature and sunlight exposure. Petal number: approximately 13 to 19 on average. Petal shape: orbicular. Petal drop: commonly the petals detach cleanly at full blossom maturity. Stamen number: commonly approximately 61 on average. Anthers: Yellow Group 6B. Filament color: Orange-Red Group 34A. Pistils: approximately 47 on average. Stigmas: Yellow-Green Group 154C in coloration. Styles: Yellow Group 4C in coloration. Receptacle: separate and free.

Development:
- *Vegetation.*—Vigorous and strong.
- *Blooming.*—Substantially continuous and everblooming.
- *Resistance to diseases.*—Highly tolerant to Black Spot and Powdery Mildew.

*Hardiness zone.*—U.S.D.A. Hardiness Zone Nos. 4 to 9.

I claim:

1. A new and distinct landscape shrub rose plant characterized by the following combination of characteristics:

(a) exhibits a dense spreading growth habit, (b) forms in clusters on a substantially continuous basis attractive semi-double bright fuschsia pink blossoms that change to apricot yellow and near white at the center, (c) forms medium green to dark green semi-glossy foliage, (d) displays high tolerance to Black Spot and Powdery Mildew; and (e) is particularly well suited for growing as attractive ornamentation in parks and gardens;

substantially as herein shown and described.

* * * * *